(12) United States Patent
Solem

(10) Patent No.: US 6,656,213 B2
(45) Date of Patent: Dec. 2, 2003

(54) STENT DELIVERY SYSTEM

(76) Inventor: Jan Otto Solem, Wallenruttistrasse 14, CH-8234 Stetten (SE)

( * ) Notice: Subject to any disclaimer, the term of this patent is extended or adjusted under 35 U.S.C. 154(b) by 98 days.

(21) Appl. No.: 09/884,155

(22) Filed: Jun. 20, 2001

(65) Prior Publication Data

US 2001/0056295 A1 Dec. 27, 2001

(30) Foreign Application Priority Data

Jun. 22, 2000 (SE) .............................. 0002395

(51) Int. Cl.[7] .................................................. A61F 2/06
(52) U.S. Cl. ...................... 623/1.11; 606/98; 606/108
(58) Field of Search .......................... 623/1.11; 606/98, 606/108, 191; 604/103.05, 96.01, 264, 104, 915, 916

(56) References Cited

U.S. PATENT DOCUMENTS

| 4,950,227 A | 8/1990 | Savin et al. |
| 5,549,635 A | 8/1996 | Solar |
| 5,948,191 A | 9/1999 | Solovay |
| 5,980,530 A | 11/1999 | Willard et al. |

*Primary Examiner*—Paul B. Prebilic
*Assistant Examiner*—Crystal Gilpin
(74) *Attorney, Agent, or Firm*—Browdy and Neimark, PLLC

(57) ABSTRACT

A stent delivery system comprises a catheter having a distal end and a proximal end, and a self expanding stent device having a compressed state and an expanded state and being positioned along the catheter and close to the distal end thereof. The stent delivery system further comprises a capsule enclosing the self-expanding stent device in its compressed state along substantially the whole length thereof. The capsule has an open distal end and a proximal end fixed to the catheter. Further, the capsule has at least one perforation extending longitudinally of said capsule from the distal end substantially to the proximal end thereof. The stent delivery system also comprises a balloon positioned within the capsule so as to break the capsule along said at least one perforation when inflated, whereby the stent device may expand to its expanded state, Thereafter the catheter with the broken capsule may be withdrawn from a duct in which the catheter has been introduced to a desired position.

14 Claims, 13 Drawing Sheets

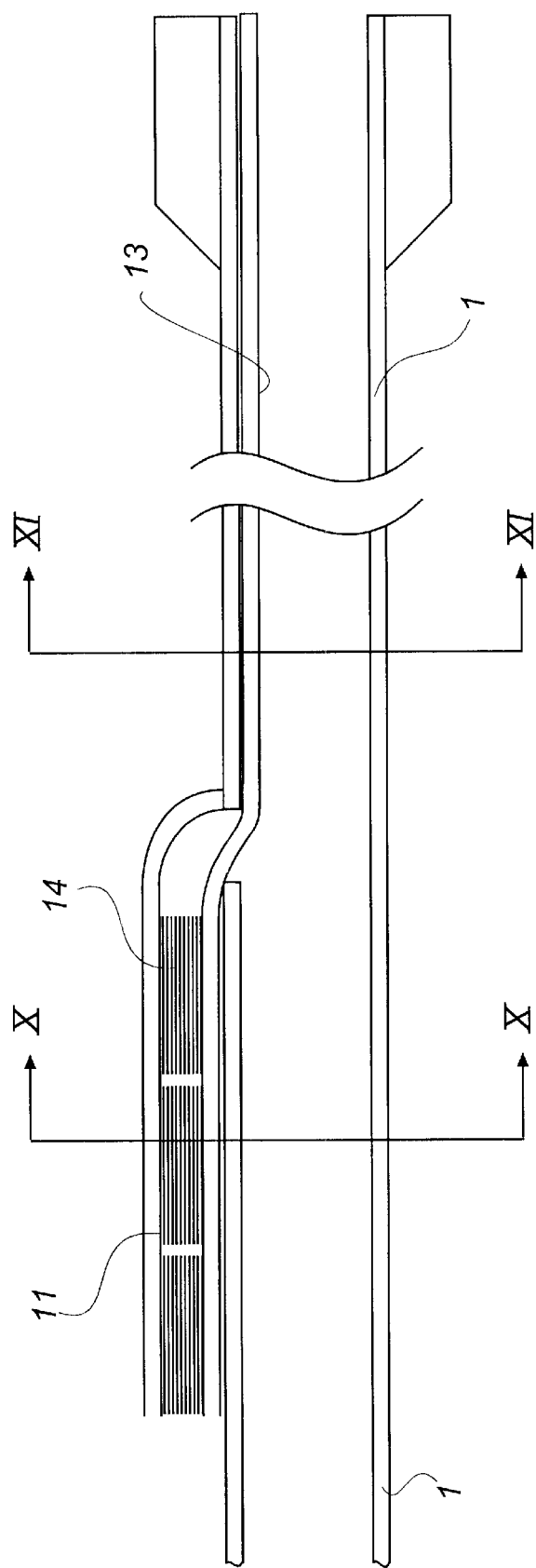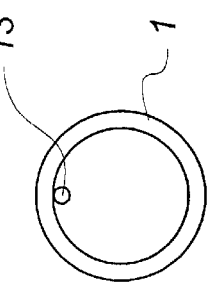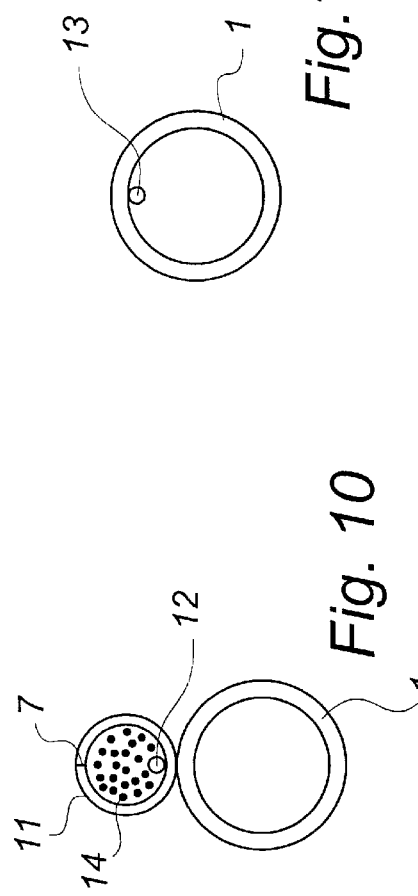

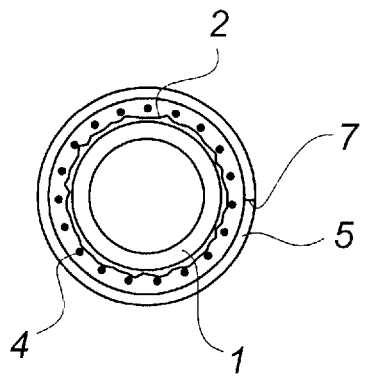
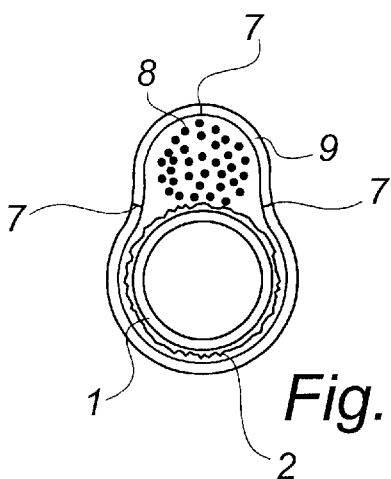
Fig. 12
Fig. 13
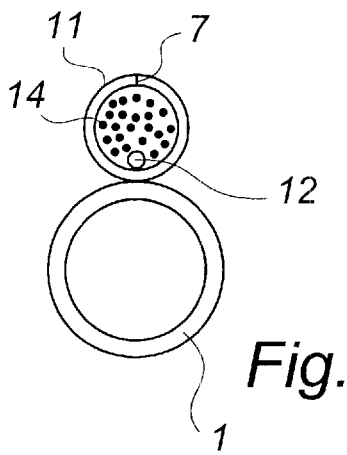
Fig. 14
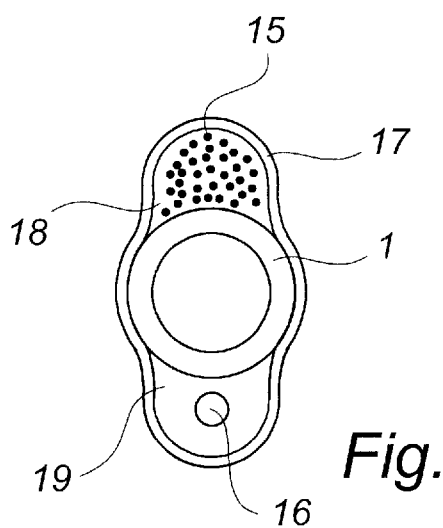
Fig. 15
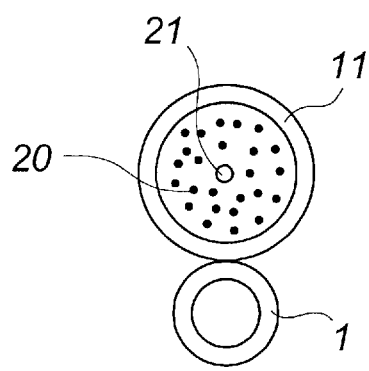
Fig. 16

STENT DELIVERY SYSTEM

BACKGROUND OF THE INVENTION

The present invention is related to a delivery system for self-expanding medical vascular devices.

Modern treatment of vascular blockage like arteriosclerosis in arteries or other abnormalities in anatomical ducts or vessels that create blockings or narrowing in the ducts, today more often comprises balloon dilatation and securing the inner vessel wall by means of metal grid cylinders, so called stents, to prevent collapse of the vessel walls after the dilatation. In other cases where there is a lesion in the duct wall causing bleeding or a risk of bleeding, covered stents or stented vascular grafts may secure such lesions.

Extremely important is the closure of such leaks in the vessels of the brain and the heart. Stents are also used to keep other ducts open in the body (e.g. the oesophagus, the bile ducts and the airway passages) that are suffering of blockages due to causes like cancer. There are also self-expanding covered stents or vascular grafts on the market. There are two main types of stents available, stents that have to be expanded by means of a balloon, i.e. pressure-expandable stents, and then the flexible self-expanding stents made of memory metals like the Nitinol stents, that will expand by themselves as a result of the inherent inner strength and memory.

The self-expanding memory metal stents have the advantage of taking the form and size of the vessel even some time after its placement and it remains flexible. The drawbacks of self-expanding stents and covered stents and covered stent grafts include the difficulty to deploy them. They will have to be restrained inside cylinders during the placement and thereafter pushed out of the restraining cylinders when the desired point is reached. The restraining cylinders and the pushing rods make the whole system bulky and stiff and thereby not suitable for small vessels and vessels on locations where the vessels are tortuous, like in the brain and in the heart.

However, U.S. Pat. No. 5,549,635 discloses a deployment apparatus for a self-expanding stent which uses a catheter, a balloon enclosing a distal part of the catheter, a self-expanding stent enclosing the balloon and two breakable retainer rings enclosing distal and proximal end portions of the self-expanding stent in a compressed state thereof. When inflating the balloon the retainer rings will get loose from the self-expanding stent which will expand. Then the catheter including the balloon and the breakable retainer rings should be withdrawn through the now expanded stent.

Since said retainer rings extend towards each other from the distal and proximal ends of the stent, there is a risk that the catheter cannot easily be withdrawn as a result of parts of the distal retainer ring being stuck between the expanded stent and the duct in which the stent is allowed to expand. Further, only a specific, substantially stiff self expanding stent may be used according to U.S. Pat. No. 5,549,635 which eliminates the use of said deployment apparatus in ducts of relatively small diameter and having a curved path and also eliminates the use of said deployment apparatus for deployment of several longitudinally spaced apart stents.

SUMMARY OF THE INVENTION

A main object of the present invention is to provide a stent delivery system and method which allow deploying of a self expanding stent also in ducts of relatively small diameters and following curved paths such that very bendable and flexible stents may be deployed.

Thus, a stent delivery system comprises a catheter having a distal end and a proximal end, and a self expanding stent device having a compressed state and an expanded state and being positioned along the catheter and close to the distal end thereof. The stent delivery system further comprises a capsule enclosing the self expanding stent device in its compressed state along substantially the whole length thereof, said capsule having an open distal end and a proximal end fixed to the catheter and further having at least one perforation extending longitudinally of said capsule from the distal end substantially to the proximal end thereof. Finally, the stent delivery system comprises a balloon positioned within the capsule so as to break the capsule along said at least one perforation. Thereby, the stent device may expand to its expanded state and the catheter with the broken capsule may be withdrawn.

In a first embodiment of the stent delivery system according to the present invention, the balloon encloses a distal part of the catheter and the stent device encloses the balloon.

In a second embodiment of the stent delivery system according to the present invention, the balloon encloses a distal part of the catheter and the stent device is positioned between the balloon and the capsule in a circumferentially limited area.

In a third embodiment of the stent delivery system according to the present invention, the balloon is positioned between the catheter and the capsule in a first, circumferentially limited area and the stent device is positioned between the catheter and the capsule in a second, circumferentially limited area.

In a fourth embodiment of the stent delivery system according to the present invention, the capsule is positioned outside the perimeter of the catheter. Then, the stent device and the balloon are preferably positioned side by side in the capsule. Alternatively, the balloon may be positioned within the stent device.

Further a stent delivery capsule device for introduction into a vessel by means of a catheter comprises a substantially cylindrical capsule having an open distal end and a closed proximal end, a self expanding stent device and a balloon, both positioned within the capsule and extending substantially along the length thereof.

Finally, a method of inserting a self expandable stent device into an anatomical duct, comprises the steps of i) providing a stent delivery system which comprises: a catheter having a distal end and a proximal end, a self expanding stent device having a compressed state and an expanded state and being positioned along the catheter and close to the distal end thereof, and a capsule enclosing the self expanding stent device in its compressed state along substantially the whole length thereof. The capsule has an open distal end and a proximal end fixed to the catheter and further has at least one perforation extending longitudinally of said capsule from the distal end substantially to the proximal end thereof, and a balloon positioned within the capsule and capable of breaking the capsule along said at least one perforation when expanded;

ii) inserting the catheter to which the capsule is fixed, into said anatomical duct and to a desired position therein;

iii) inflating the balloon such that the capsule is ruptured and the stent device is expanded to its expanded state engaging an inner surface of the duct; and iv) withdrawing the catheter and the capsule fixed thereto from said desired position in the duct, whereby the stent device is deployed at the desired position in the duct.

The delivery system according to the invention can be made with small diameters. The system permits a more precise placement of the stent in the vessel than the prior systems relying on release from the system by pushing or movement in the axial direction of the catheter.

The delivery system according to the invention is also advantageous as compared to the delivery system of U.S. Pat. No. 5,549,635 in that it has a high flexibility and is soft so that it may enter tortuous vessels without damaging the vessel wall. Inside the capsule self-expanding devices with a great variety of forms may be used. Thereby tailored special devices having branches, ends sticking out, umbrella shape and any other shape may be restrained within the capsule during delivery. Further, the capsule may be produced together with the device as an integrated part thereof and later assembled to the catheter.

BRIEF DESCRIPTION OF THE DRAWINGS

FIG. 9 is a longitudinal sectional view of a third embodiment of a stent delivery system according to the present invention.

FIG. 10 is a cross-sectional view along the line X—X in FIG. 9.

FIG. 11 is a cross-sectional view along the line XI—XI in FIG. 9.

FIGS. 12–16 are cross-sectional views illustrating five different embodiments of a stent delivery system according to the present invention (FIGS. 12, 13 and 14 being identical to FIGS. 2, 8 and 10, respectively).

DESCRIPTION OF PREFERRED EMBODIMENTS

Figure 1:
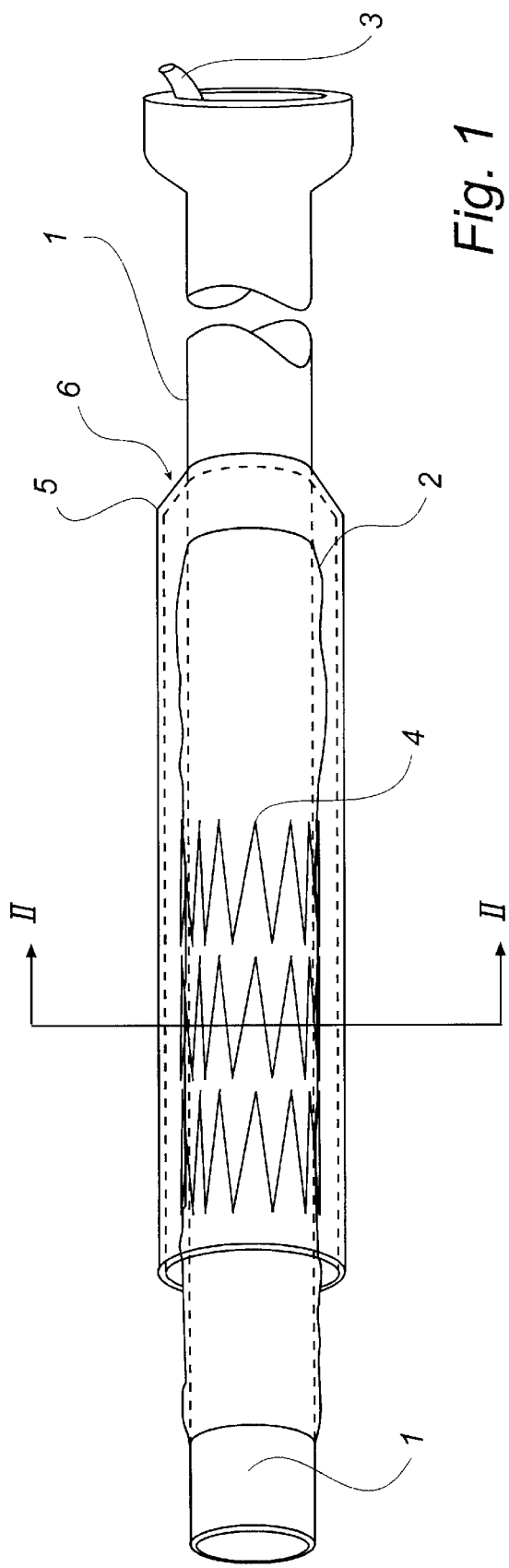
FIG. 1 is a longitudinal sectional view of a first embodiment of a stent delivery system according to the present invention.
Figure 2:
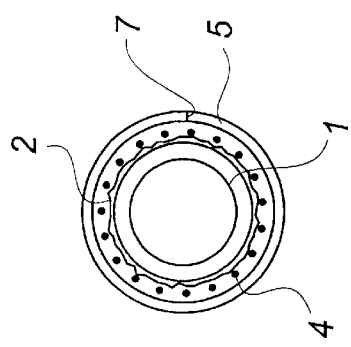
FIG. 2 is a cross-sectional view along the line II—II in FIG. 1.

Referring to FIGS. 1–4, a first embodiment of a stent delivery system according to the invention comprises a cardiac catheterisation catheter 1 or any other vascular interventional catheter with a balloon 2 enclosing a distal part of the catheter 1. The catheter 1 has a separate lumen 3 extending from the proximal end of the balloon 2 to the proximal end of the catheter 1. This lumen 3 is used for inflating and deflating the balloon 2 which is shown in its deflated state in FIG. 1.

A self expanding stent device 4, e.g. a stent, a covered stent or a stent graft, is positioned on and substantially enclosing the balloon 2. It is held in a compressed state by an enclosing tube or capsule 5. Basically, this capsule 5 is a cylinder preferably made of a synthetic, plastic material, e.g. expanded polytetrafluoroethylen (PTFE), polyvinyl, polyurethan or any other synthetic material. A proximal end part 6 of the capsule 5 is a ring of reduced diameter so as to fit tightly on the interventional catheter 1 and thus being fixed thereto.

Figure 3:
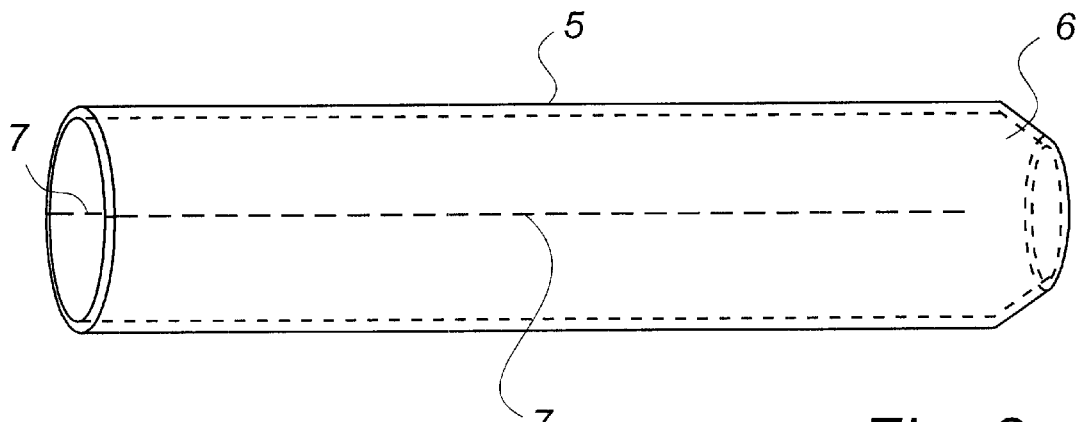
FIG. 3 is an elevational view of a capsule shown in FIG. 1.
Figure 4:
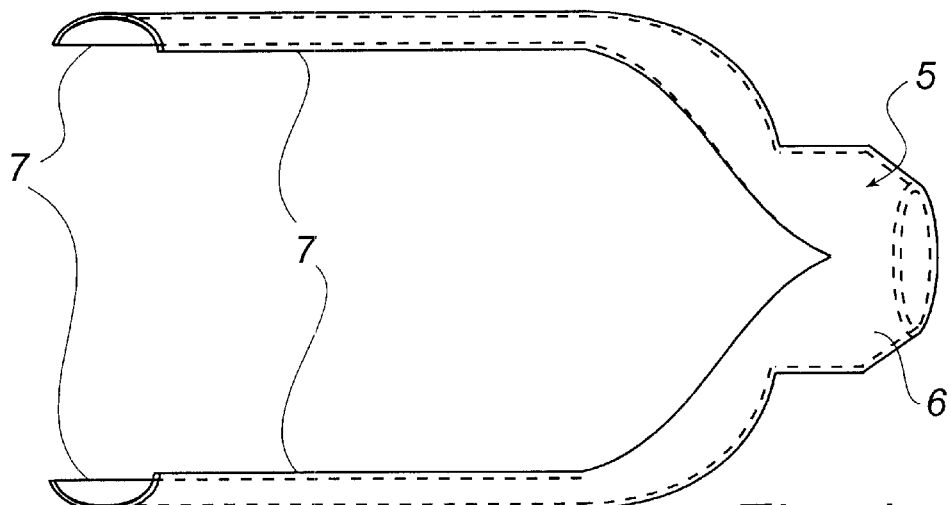
FIG. 4 is an elevational view of the capsule in FIG. 3 when ruptured.

A most important feature of this capsule 5 is a longitudinal perforation line 7 that will result in a fracture of the wall of the capsule 5 when the balloon 2 is inflated to release the self expanding stent device 4 inside the capsule 5. As illustrated in FIGS. 3 and 4, the capsule 5 will transform from its state (FIG. 3) keeping the stent 4 compressed to its ruptured state (FIG. 4) being split into two strips along its length from the distal end thereof to the non-ruptured ring 6 thereof at the proximal end of the capsule 4.

Figure 5:
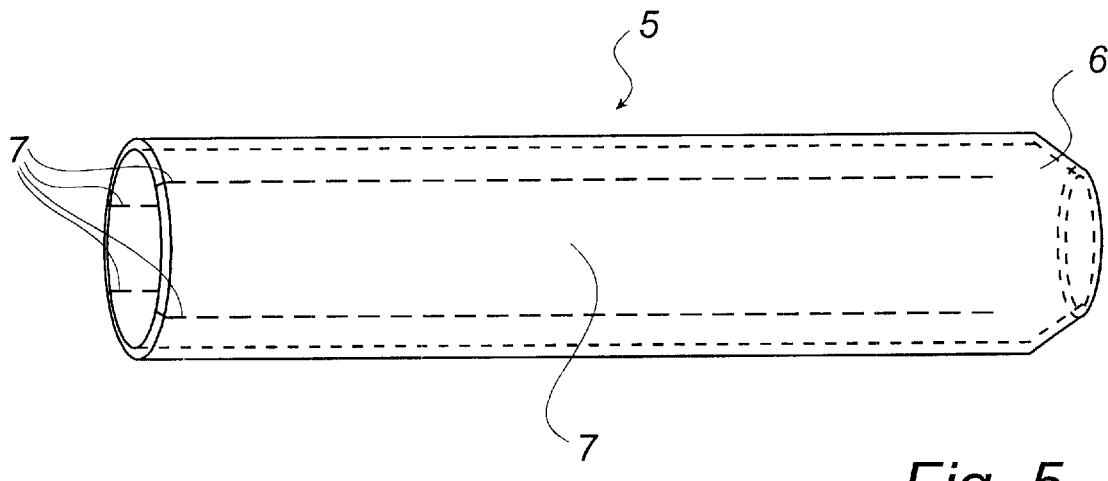
FIG. 5 is an elevational view of an alternative embodiment of the capsule shown in FIG. 3
Figure 6:
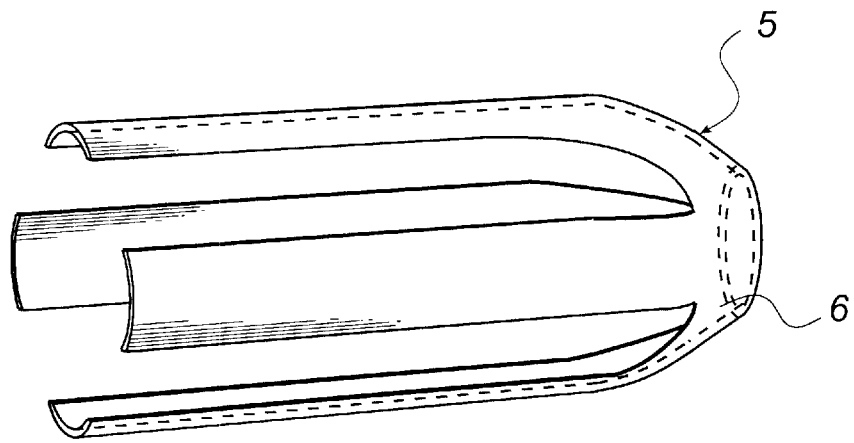
FIG. 6 is an elevational view of the capsule in FIG. 5 when ruptured.

The capsule 5 may have a single perforation line 7, two perforation lines 7, as shown in FIGS. 3 and 4, or a multiple perforation lines 7, as illustrated by a second embodiment of the capsule in FIGS. 5 and 6. As a result the ruptured capsule, i.e. after inflation of the balloon, will have different shapes with one or more stripes of material extending from a non-ruptured proximal end 6 of the capsule 5 to the open distal end of the capsule 5.

The capsule 5 may be fixed on the interventional catheter 1 outside of the balloon 2 by gluing the narrow proximal end part 6 to the perimeter of the catheter 1 at a position proximal of the balloon 2.

Figure 7:
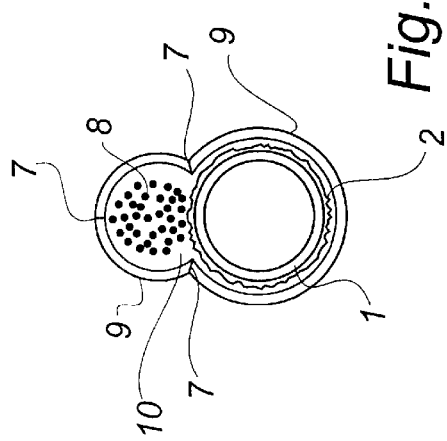
FIG. 7 is a longitudinal sectional view of a second embodiment of a stent delivery system according to the present invention.
Figure 8:
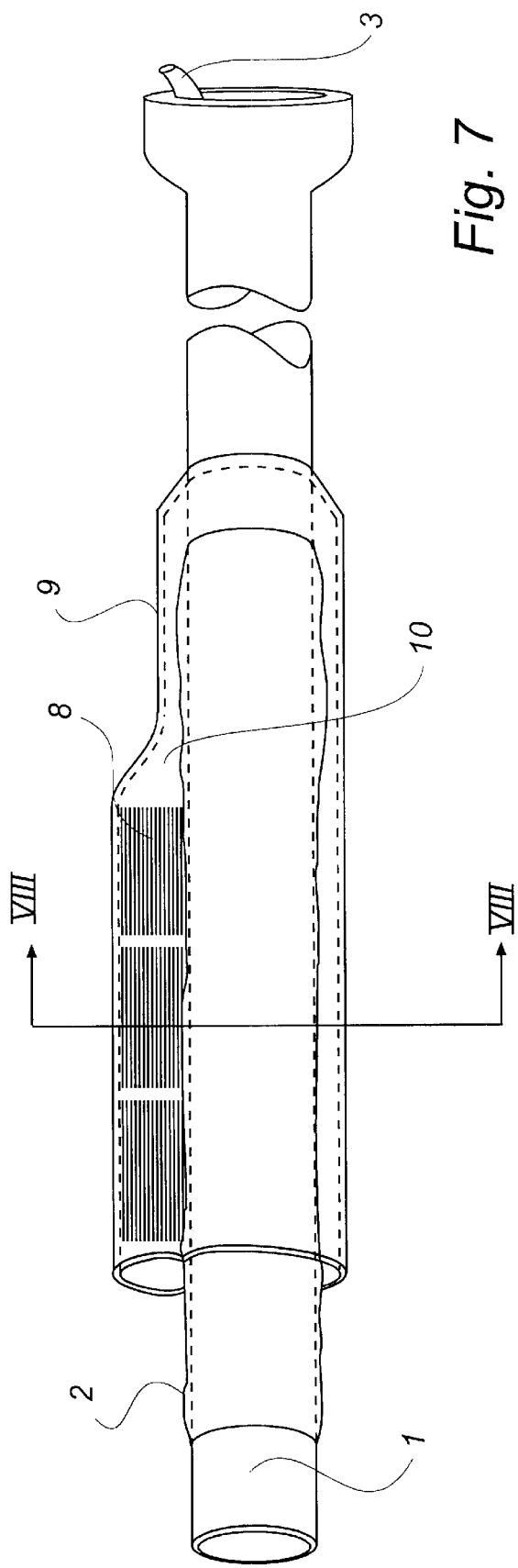
FIG. 8 is a cross-sectional view along the line VIII—VIII in FIG. 7.

Referring to FIGS. 7 and 8, a second embodiment of the delivery system has a self-expanding stent 8 positioned outside the catheter 1 and the balloon 2 but still inside a capsule 9 which keeps the stent 8 in its compressed state. Thus, the capsule 9 defines a pocket 10 outside the catheter 1, and the balloon 2 lies within a circumferentially limited area.

The capsule 9 may have a single perforation line 7 located on its top and/or perforation lines 7 located on its sides, as seen in FIG. 8.

Referring to FIGS. 9, 10 and 11, a third embodiment of the delivery system has a capsule 11 which does not enclose the interventional catheter 1 but is positioned outside and along the interventional catheter 1. This capsule 11 may have a smaller diameter than the capsule 5 and 9 according to the first and second embodiments, respectively, as it is not depending of the dimension of the catheter 1. Thus, this capsule 11 sits on top of the interventional catheter 1 like a backpack. In this configuration the interventional catheter 1 does not have any balloon since a balloon 12 is located within the capsule 11 itself. This smaller balloon 12 has its own small lumen 13 connected to the proximal end of the catheter 1 and running through (as shown in FIGS. 9 and 11) or on the outside of the interventional catheter 1 for inflation and deflation of the small deployment balloon 12 inside the capsule 11. A stent, covered stent or a covered stent graft 14 is inserted inside the small capsule 11 side by side with the balloon 12, i.e. between the capsule wall and the balloon 12 inside the capsule 11. By inflation of the small balloon 12 inside the capsule 11 sitting on top of the catheter 1 a single perforation line 7 provided on top of the capsule 11 will open the capsule 11 longitudinally such that the self expanding device 14 can expand and deploy itself.

An important advantage of the small backpack capsule 11 is that it may be produced separately from the catheter 1 together with the stent 14 and assembled to the catheter 1 at a later stage.

FIGS. 12–16 schematically depict a summary of five different embodiments of the deliver system according to the present invention. The embodiments in FIGS. 12, 13 and 14 correspond to the first, second and third embodiments, as is evident from a comparison with FIGS. 2, 8 and 10, respectively. In a fourth embodiment illustrated in FIG. 15, a stent 15 and a balloon 16 are positioned outside the catheter 1 and inside a capsule 17, each one in a circumferentially limited area within a pocket 18, 19 defined by the capsule 17. The two pockets 18, 19 may be positioned apart from each other circumferentially or close together so as to form a single pocket. In a fifth embodiment illustrated in FIG. 16, a capsule 11 is positioned outside the catheter 1, as in the above-described third embodiment, and encloses both a stent 20 and a small deployment balloon 21. However, in this embodiment the balloon 21 is positioned inside the stent 20 enabling the use of either a self-expanding stent or a pressure-expanded stent.

Figure 17:
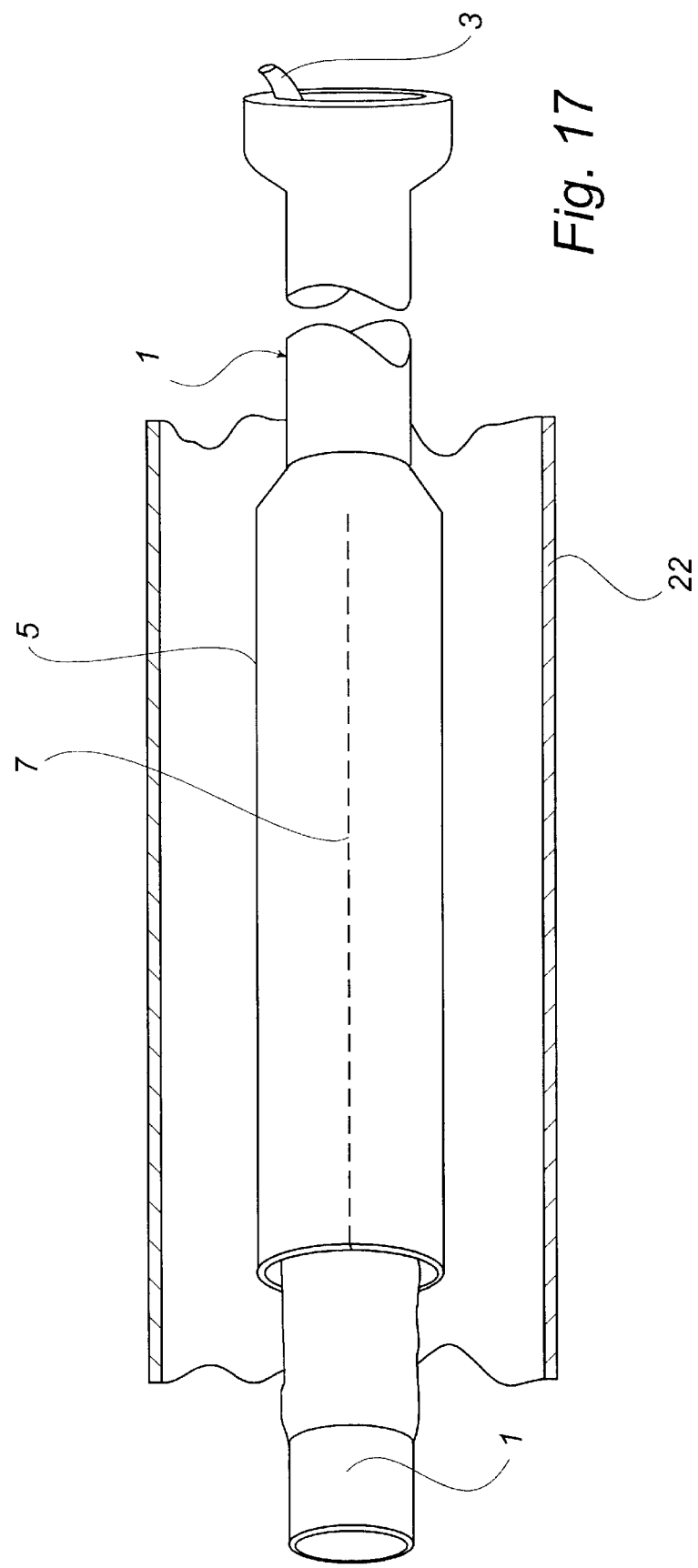
FIGS. 17–19 illustrate the deployment of the first embodiment of a stent delivery system according to the present invention.
Figure 18:
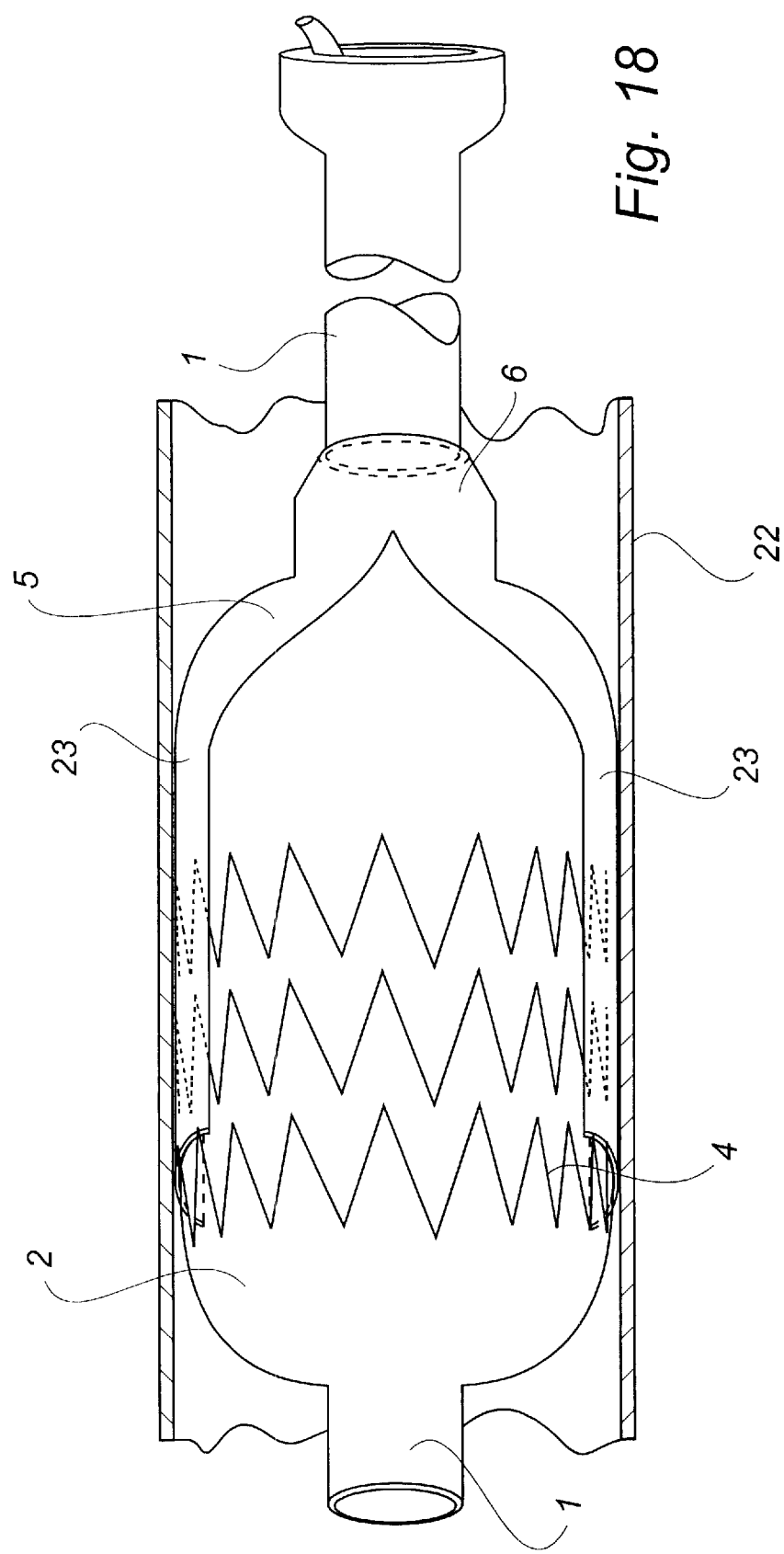
Figure 19:
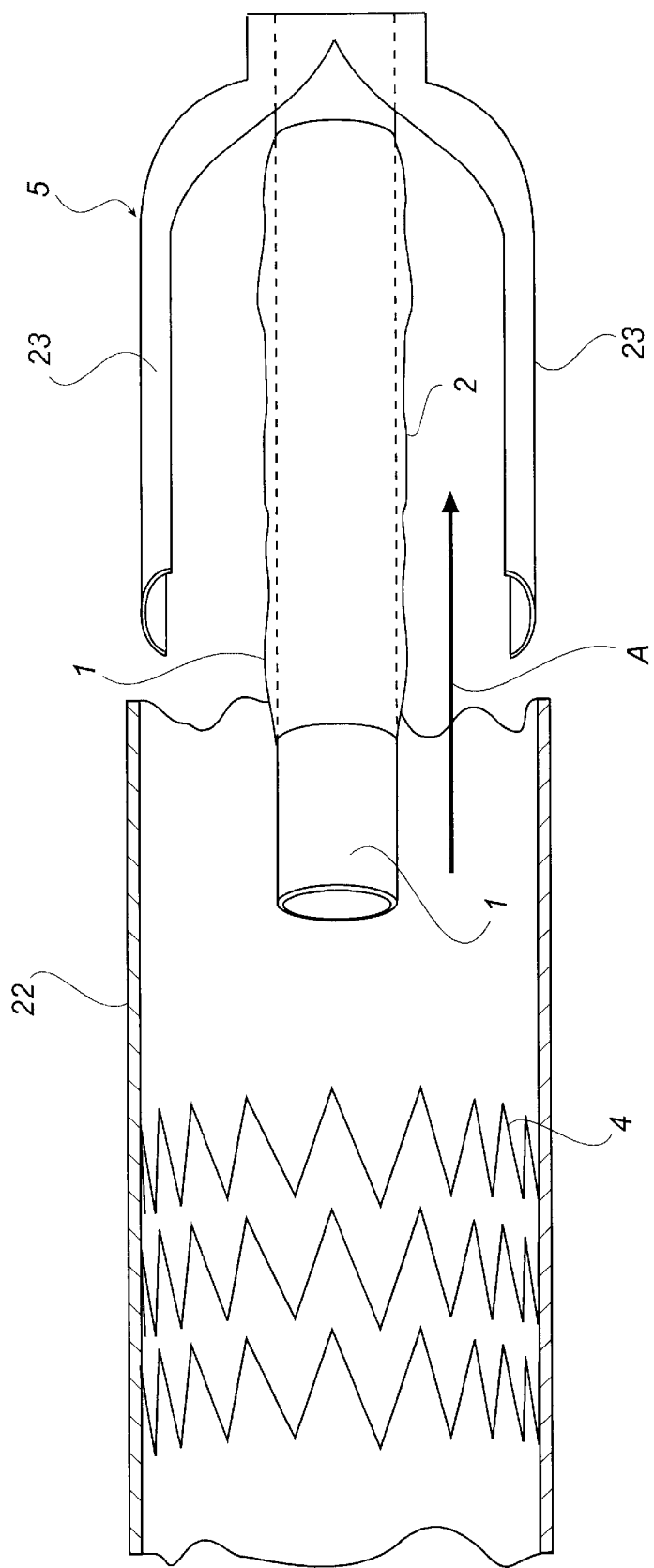

Referring to FIGS. 17–19, a method of inserting a self expandable stent using the first embodiment will be described.

The catheter 1 is placed inside the wall of a vessel 22 at the intended location for the deployment of the self-expanding device 4, cf. FIG. 17. Then the balloon 2 is inflated such that the capsule 5 will open along the perforation lines 7 and the stent 4 will expand to engagement with the vessel wall at the correct position, cf. FIG. 18. There are now two small remaining strips 23 of the capsule present between the vessel wall and the stent 4. Now, the balloon 2 is deflated and the catheter 1 is retracted. The two strips 23 are only a fraction of the size of the expanded stent 4 and shorter than the stent 4 and will easily follow the catheter 1 out when this is retracted in the direction of an arrow A, cf. FIG. 19.

Figure 20:
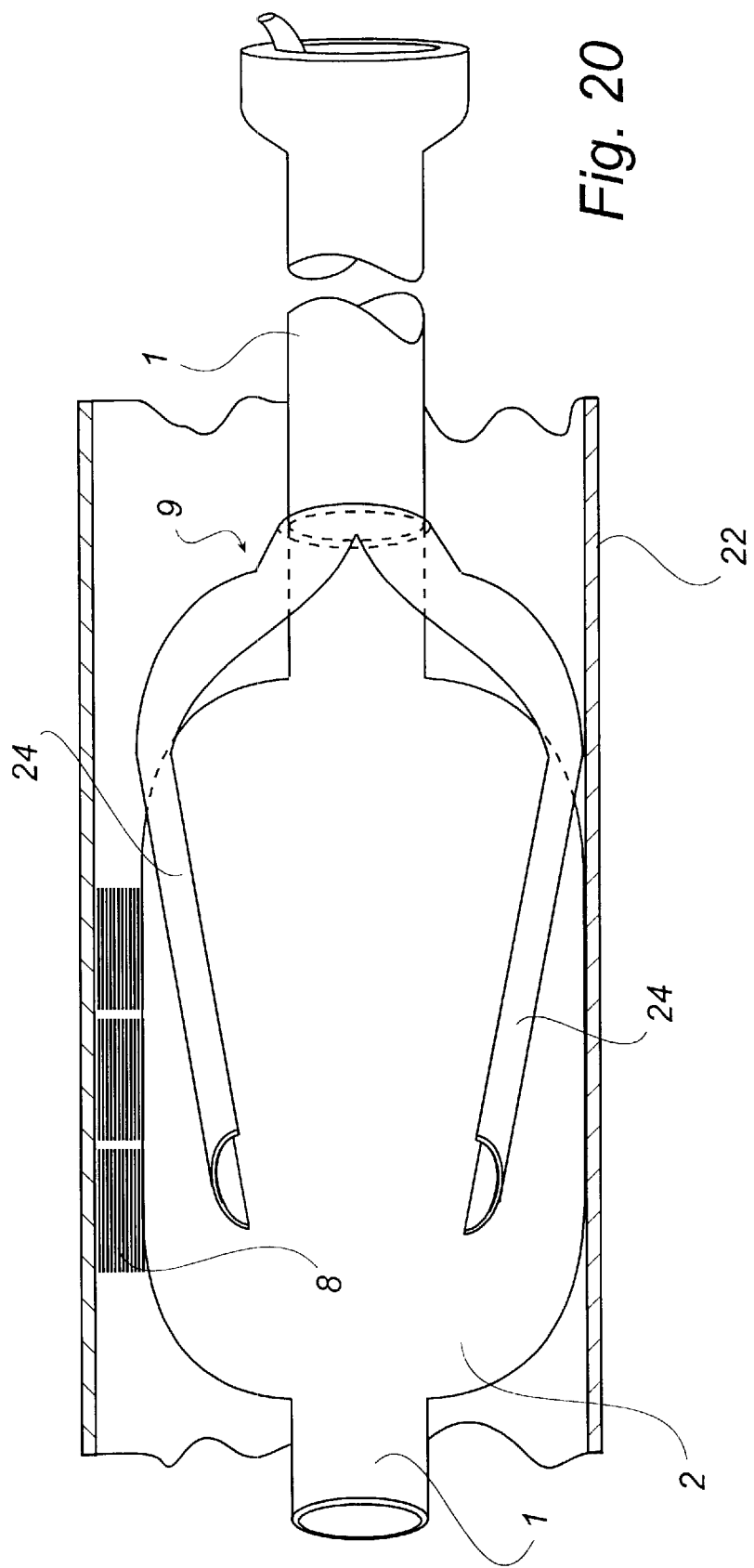
FIGS. 20 and 21 illustrate the deployment of the second embodiment of a stent delivery system according to the present invention.
Figure 21:
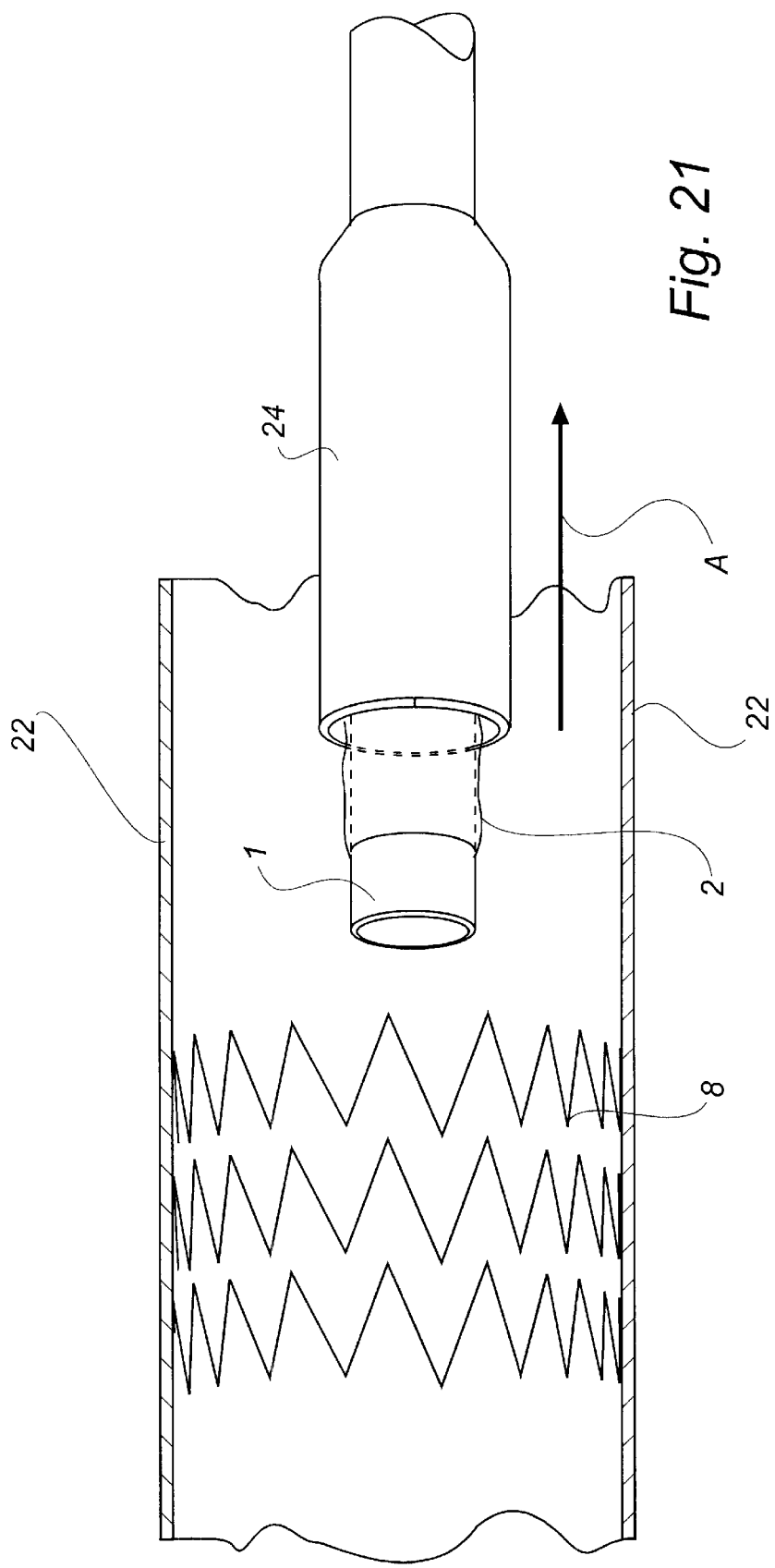

Referring to FIGS. 20–21, a method of inserting a self-expandable stent using the second embodiment will be described.

In FIG. 20 the second embodiment, illustrated in FIG. 7, is shown introduced into a vessel 22 and with the balloon 2 inflated. Consequently, the capsule 9 has broken along the two perforation lines 7 at the side of the balloon 2. Thus, the capsule 9 is open and the stent 8 is positioned at correct position in the vessel 22. However, the stent 8 will not expand until the balloon 2 is deflated. Two small remaining strips 24 of the capsule 9 will follow the catheter 1 when this is retracted in the direction of an arrow A, as showed in FIG. 21.

Figure 22:
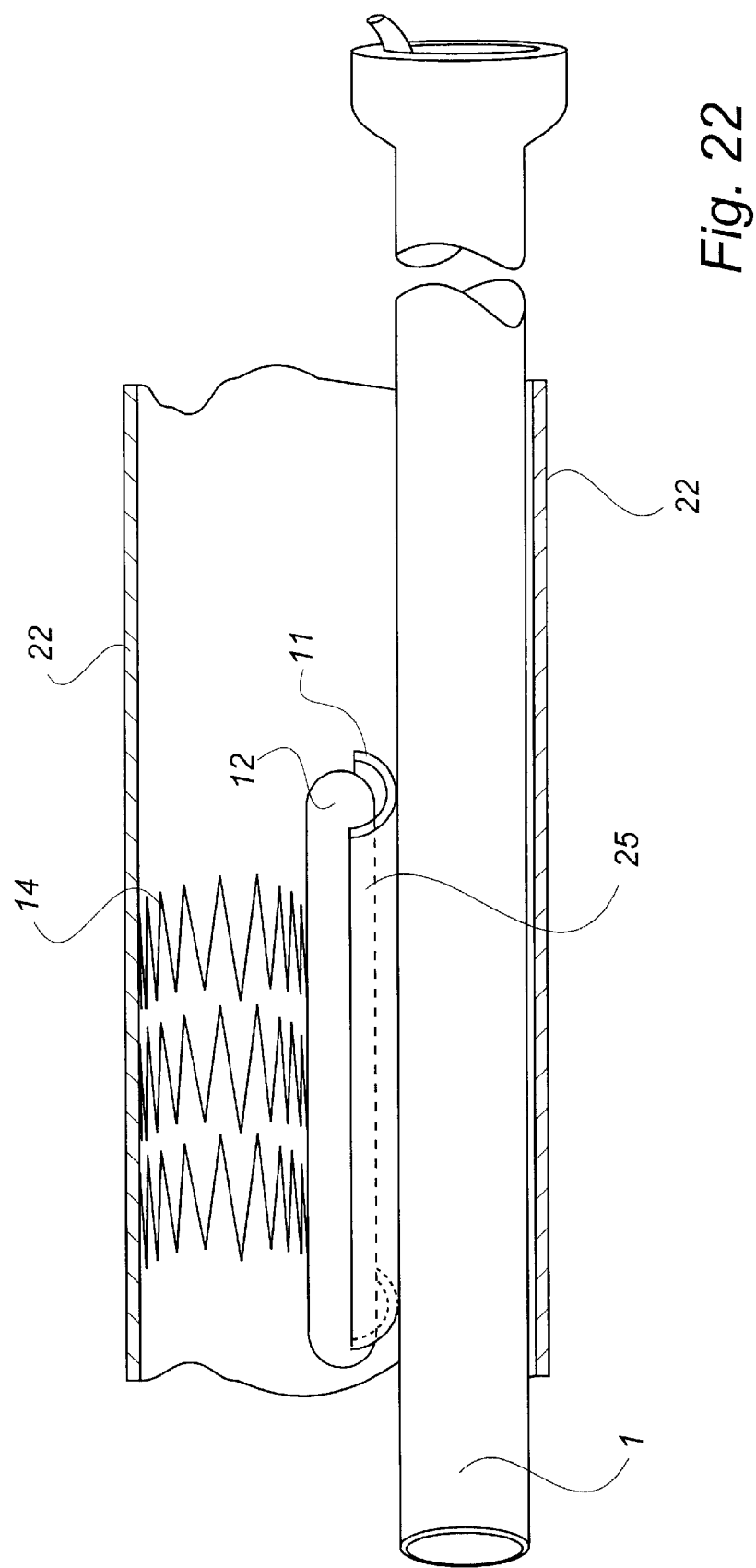
FIGS. 22 and 23 illustrate the deployment of the third embodiment of a stent delivery system according to the present invention.
Figure 23:
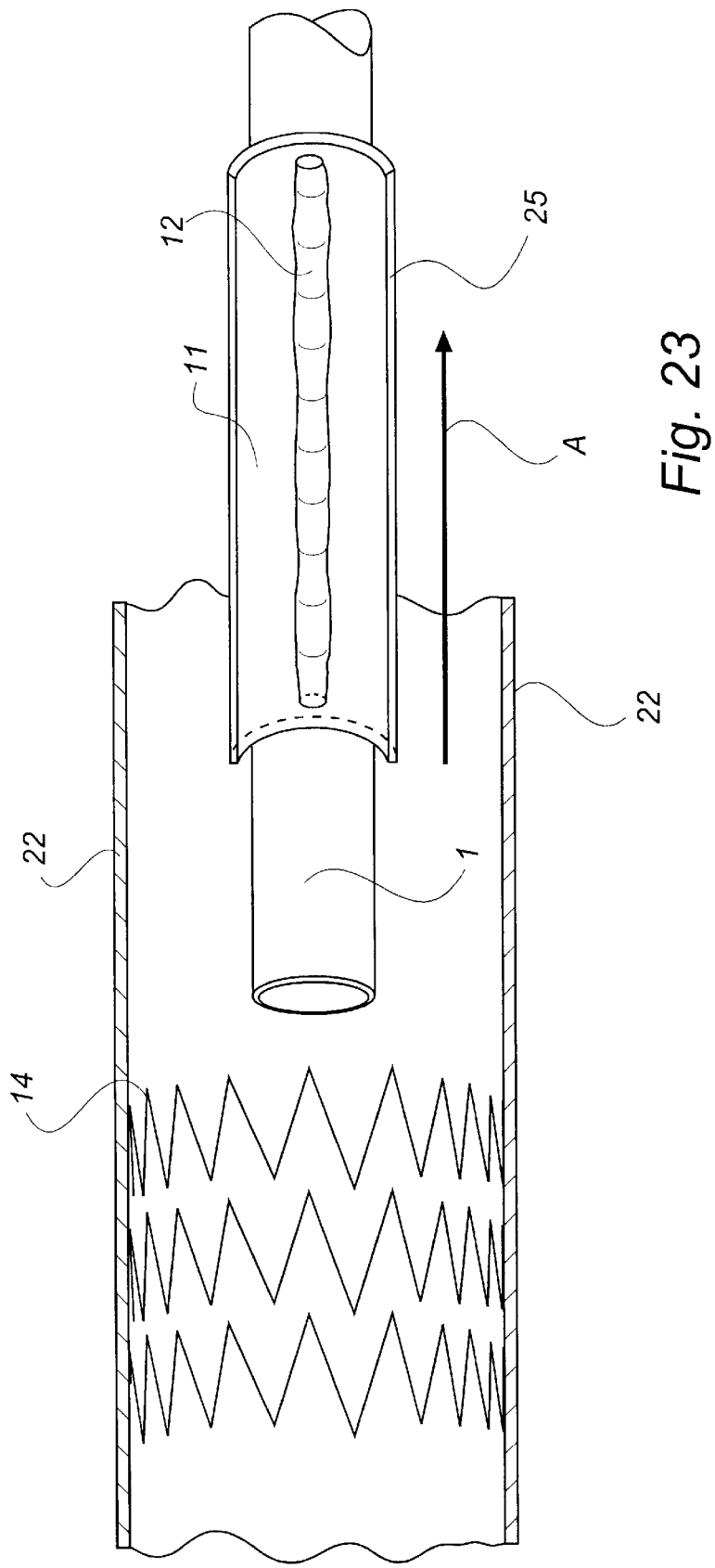

Referring to FIGS. 22–23, a method of inserting a self expandable stent using the third embodiment will be described.

In FIG. 22 the third embodiment, illustrated in FIGS. 9–11, is shown introduced into a vessel 22 and with the balloon 12 inflated. Consequently, the capsule 11 has broken along the single perforation line 7 at the top of the capsule 11. Thus, the capsule 11 is open and the stent 14 is positioned at correct position in the vessel 22. The stent 14 will expand partially and press the catheter 1 with the capsule 11 against the vessel wall. Thus, the stent 14 will not expand completely until the balloon 12 is deflated and the catheter 1 withdrawn. After deflation of the balloon 12 the catheter 1 and the opened capsule 11 are retracted out of the vessel. The remaining strip 25 of the capsule 11 will follow the catheter 1 when this is retracted in the direction of an arrow A, as showed in FIG. 23, and the self-expanding stent 14 will now expand completely.

A completely new deployment system for release of self-expanding medical devices is presented. The self-expanding device is restrained inside a soft, flexible capsule located outside of a catheter as a backpack or around a catheter. The capsule has the special feature of a perforation line. By inflating a balloon the perforation line is broken and the device is deployed and may expand.

It is to be understood that modifications of the above-described stent delivery systems and methods can be made by people skilled in the art without departing from the spirit and scope of the invention. Thus, the distal ends of the catheter, the balloon, the stent device and the capsule may be bifurcated so as to fit into a bifurcation of a vessel. Also, the stent may be divided into several longitudinally separated sections.

What is claimed is:

1. A stent delivery system comprising
 a catheter having a distal end and a proximal end,
 a self expanding stent device having a compressed state and an expanded state and being positioned along the catheter and close to the distal end thereof,
 a capsule enclosing the self expanding stent device in its compressed state, said capsule having an open distal end and a proximal end fixed to the catheter and further having at least one perforation extending longitudinally of said capsule from the distal end thereof substantially to the proximal end thereof, and
 a balloon positioned within the capsule so as to break the capsule along said at least one perforation,
 whereby the stent device may expand to its expanded state and the catheter with the broken capsule may be withdrawn, and
 wherein the catheter is arranged outside the self expanding stent device in a side-by-side relationship therewith.

2. The stent delivery system according to claim 1, wherein the balloon encloses a distal part of the catheter and the stent device is positioned between the balloon and the capsule in a circumferentially limited area.

3. The stent delivery system according to claim 1, wherein the balloon is positioned between the catheter and the capsule in a first, circumferentially limited area and the stent device is positioned between the catheter and the capsule in a second, circumferentially limited area.

4. The stent delivery system according to claim 1, wherein the catheter is arranged outside the capsule in a side-by-side relationship therewith.

5. The stent delivery system according to claim 4, wherein the stent device and the balloon are positioned alongside each other in the capsule.

6. The stent delivery system according to claim 4, wherein the balloon is positioned within the stent device.

7. The stent delivery system according to claim 4, wherein the capsule is fixed to the catheter along an axial contact line between them.

8. The stent delivery system according to claim 5, wherein the capsule is fixed to the catheter along an axial contact line between them.

9. The stent delivery system according to claim 1, comprising a lumen extending from a proximal end of the balloon to the proximal end of the catheter.

10. The stent delivery system according to claim 1, wherein the distal ends of the catheter, the balloon, the stent device and the capsule are bifurcated.

11. A stent delivery capsule device for introduction into a vessel by means of a catheter, said capsule device being arranged to be carried, during said introduction, by the catheter in a side-by-side relationship therewith, the catheter being arranged outside the capsule device, said capsule device comprising a substantially cylindrical capsule having an open distal end and a closed proximal end, a self expanding stent device and a balloon, said self expanding stent device and said balloon both being positioned within the capsule and extending substantially along the length thereof, said capsule having at least one axially extending perforation that will break when the balloon is inflated, whereby the self-expanding stent device may expand to an expanded state and the capsule and the balloon may be withdrawn by means of the catheter.

12. The stent delivery capsule device according to claim 11, wherein the stent device and the balloon are positioned alongside each other in the capsule.

13. The stent delivery capsule device according to claim 11, wherein the balloon is positioned within the stent device.

14. A method of inserting a self expandable stent device into an anatomical duct, comprising the steps of i) providing a stent delivery system which comprises:
   a catheter having a distal end and a proximal end,
   a self expanding stent device having a compressed state and an expanded state and being positioned along the catheter and close to the distal end thereof,
   a capsule enclosing the self expanding stent device in its compressed state, said capsule having an open distal end and a proximal end fixed to the catheter and further having at least one perforation extending longitudinally of said capsule from the distal end thereof substantially to the proximal end thereof, and
   a balloon positioned within the capsule and capable of breaking the capsule along said at least one perforation when expanded,
   wherein the catheter is arranged outside the self expanding stent device in a side-by-side relationship therewith;

ii) inserting the catheter to which the capsule is fixed, into said anatomical duct and to a desired position therein;

iii) inflating the balloon such that the capsule is ruptured and the stent device is expanded to its expanded state engaging an inner surface of the duct; and iv) withdrawing the catheter and the capsule fixed thereto from said desired position in the duct, whereby the stent device is deployed at the desired position in the duct.

* * * * *